(12) United States Patent
Hamied et al.

(10) Patent No.: US 7,022,698 B2
(45) Date of Patent: Apr. 4, 2006

(54) PHARMACEUTICAL COMPOSITIONS CONTAINING NEW POLYMORPHIC FORMS OF OLANZAPINE AND USES THEREOF

(75) Inventors: Yusuf K. Hamied, Mah (IN); Rajendra N. Kankan, Mah (IN); Dharmaraj R. Rao, Mah (IN)

(73) Assignee: U & I Pharmaceuticals, Ltd., Whitestone, NY (US)

( * ) Notice: Subject to any disclaimer, the term of this patent is extended or adjusted under 35 U.S.C. 154(b) by 312 days.

(21) Appl. No.: 10/026,949

(22) Filed: Dec. 27, 2001

(65) Prior Publication Data

US 2002/0165225 A1 Nov. 7, 2002

Related U.S. Application Data

(63) Continuation-in-part of application No. 09/540,749, filed on Mar. 31, 2000, now Pat. No. 6,348,458.

(30) Foreign Application Priority Data

Dec. 28, 1999 (IN) .......................... 972/BOM/1999
Dec. 28, 1999 (IN) .......................... 977/BOM/1999

(51) Int. Cl.
A61K 31/55 (2006.01)
A61P 25/18 (2006.01)
C07D 495/04 (2006.01)

(52) U.S. Cl. ...................................... 514/220; 540/557
(58) Field of Classification Search ................ 514/220; 540/557
See application file for complete search history.

(56) References Cited

U.S. PATENT DOCUMENTS

| | | | |
|---|---|---|---|
| 4,115,568 A | 9/1978 | Chakrabarti et al. | 424/250 |
| 4,115,574 A | 9/1978 | Chakrabarti et al. | 424/250 |
| 5,229,382 A | 7/1993 | Chakrabarti et al. | 514/220 |
| 5,457,101 A | 10/1995 | Greenwood et al. | 514/220 |
| 5,605,897 A | 2/1997 | Beasley, Jr. et al. | 514/220 |
| 5,627,178 A | 5/1997 | Chakrabarti et al. | 514/220 |
| 5,631,250 A | 5/1997 | Bunnell et al. | 514/220 |
| 5,637,584 A | 6/1997 | Larsen | 514/220 |
| 5,696,115 A * | 12/1997 | Rasmussen | 514/220 |
| 5,703,232 A | 12/1997 | Bunnell et al. | 540/557 |
| 5,736,541 A | 4/1998 | Bunnell et al. | 514/220 |
| 5,817,655 A | 10/1998 | Chakrabarti et al. | 514/220 |
| 5,817,656 A | 10/1998 | Beasley, Jr. et al. | 514/220 |
| 5,817,657 A | 10/1998 | Beasley, Jr. et al. | 514/220 |
| 5,919,485 A | 7/1999 | Cochran et al. | 424/480 |
| 6,251,895 B1 | 6/2001 | Larsen et al. | 514/220 |

FOREIGN PATENT DOCUMENTS

| | | |
|---|---|---|
| EP | 0733635 | 9/1996 |
| EP | 0831097 | 3/1998 |
| WO | WO 0018408 | 4/2000 |

OTHER PUBLICATIONS

Houben-Weyl, "Methoden der organischen Chemie, Band I/1, Allgemeine Laboratoriumsprazis I" 1958, Georg Thieme Verlag, Stuttgart XP002163768, pp. 381-382.
R. Narendran et al. "Olanzapine Therapy in Treatment-Resistant Psychotic Mood Disorders: A Long-Term Follow-Up Study", J Clin Psychiatry. 62:7, Jul. 2001, pp. 509-516.
J. Kando et al. "Olanzapine: A new Antipsychotic Agent with Efficacy in the Management of Schizophrenia", The Annals of Pharmacotherapy. Nov., 1997, vol. 31, pp. 1325-1334.
P. Tran et al. "Double-Blind Comparison of Olanzapine Versus Risperidone in the Treatment of Schizophrenia and Other Psychotic Disorders", Journal of Clinical Psychopharmacology. vol. 17, No. 5, pp. 407-418, 1997.
F. Bymaster et al. "In Vitro and In Vivo Biochemistry of Olanzapine: A Novel, Atypical Antipsychotic Drug", J Clin Psychiatry. 1997; 58 (suppl 10), pp. 28-36.
C. Beasley et al. "Efficacy of Olanzapine: An Overview of Pivotal Clinical Trials", J Clin Psychiatry. 1997; 58 (suppl 10), pp. 7-12.
W. Glazer. "Olanzapine and the New Generation of Antipsychotic Agents: Patterns of Use", J Clin Psychiatry. 1997; 58 (suppl 10), pp. 18-21.
The Medical Letter, "On Drugs and Therapeutics". Jan. 17, 1997, vol. 38 (Issue 992), pp. 5-6.
C. Nemeroff. "Dosing the Antipsychotic Medication Olanzapine", J Clin Psychiatry. 1997; 58 (suppl 10), pp. 45-49.

(Continued)

Primary Examiner—Brenda Coleman
(74) Attorney, Agent, or Firm—Venable LLP; Julie Petruzzelli; Keith G. Haddaway (57) ABSTRACT

Pharmaceutical compositions containing Form III, Form IV, Form V olanzapine and/or pharmaceutically acceptable salts thereof. The pharmaceutical compositions are useful for the treatment of psychotic conditions, mild anxiety and gastrointestinal conditions. In particular, the compositions are useful for treating schizophrenia and related disorders, acute mania, Bipolar I Disorder, psychotic mood disorder and psychosis in patients with Alzheimer's disease.

19 Claims, 6 Drawing Sheets

OTHER PUBLICATIONS

C. Guille et al. "A Naturalistic Comparison of Clozapine, Risperidone, and Olanzapine in the Treatment of Bipolar Disorder", *J Clin Psychiatry.* 61:9, Sep. 2000, pp. 638-642.

W. Clark et al. "The Effects of Olanzapine in Reducing the Emergence of Psychosis Among Nursing Home Patients with Alzheimer's Disease", *J Clin Psychiatry.* 62:1, Jan. 2001, pp. 34-39.

K. Littrell et al. "Switching Clozapine Responders to Olanzapine", *J Clin Psychiatry.* 61:12, Dec. 2000, pp. 912-915.

J. Gomez et al. "Superior Efficacy of Olanzapine Over Haloperidol: Analysis of Patients with Schizophrenia From a Multicenter international Trial", *J Clin Psychiatry.* 2001: 62, (suppl 2), pp. 6-10.

M. Tohen et al. "Olanzapine Versus Placebo in the Treatment of Acute Mania", *Am J Psychiatry.* 156:5, May 1999, pp. 702-709.

Drugs of the Future, *Olanzapine,* 1994, vol. 19(2), pp. 114-117.

Chakrabarti et al., *4-Piperazinyl-10H-thieno[2,3-b][1,5] benzodiazepines as Potential Neuroleptics,* J. Med. Chem, 1980, vol. 23, pp. 878-884.

Chakrabarti, et al., *10-Piperazinyl-4H-thieno[3,2-b][1-5]- and -[3,4-b][1,5]benzodiazepines as Potential Neuroleptics,* J. Med. Chem. 1980, vol. 23, 884-889.

Chakrabarti, et al., *Effects of Conformationally Restricted 4-Piperazinyl-10H-thienobenzodiazepine Neuroleptics on Central Dopaminergic and Cholinergic Systems,* J. Med. Chem., 1982, vol. 25, pp. 1133-1140.

Schmitt et al., Targeting Nicotinic Acetylcholine Receptors: Advances in Molecular Design and Therapies, Annual Reports in Medicinal Chemistry, vol. 35, pp. 41-51, 2000.*

* cited by examiner

PHARMACEUTICAL COMPOSITIONS CONTAINING NEW POLYMORPHIC FORMS OF OLANZAPINE AND USES THEREOF

RELATED APPLICATIONS

This application is a continuation-in-part of U.S. application Ser. No. 09/540,749, filed Mar. 31, 2000 now U.S. Pat. No. 6,348,458, which is incorporated by reference herein in its entoirety.

BACKGROUND OF THE INVENTION

1. Field of the Invention

This invention relates to novel forms of 2-methyl-4-(4-methyl-1-piperazinyl)-10H-thieno-[2,3b][1,5] benzodiazepine (Formula A), also known as olanzapine. More specifically, the invention provides novel forms of solvate free olanzapine, methods for preparing the novel forms of olanzapine and pharmaceutical formulations containing the novel forms of olanzapine.

A

2. Background

As described in U.S. Pat. No. 5,736,541 (hereinafter "the '541 patent"), which is incorporated herein by reference in its entirety, the synthesis of olanzapine according to the methods described in U.S. Pat. No. 5,229,382, incorporated herein by reference in its entirety, produces a metastable, dull colored product referred to in the '541 patent as "Form I." The '541 patent is herein incorporated by reference in its entirety. The '541 patent discloses and claims a more stable polymorphic form of olanzapine, designated as "Form II", a method to produce "Form II" olanzapine, and pharmaceutical compositions containing "Form II" olanzapine. "Form I" and "Form II" olanzapine are characterized in the '541 patent by powder X-ray diffraction. The interplanar spacings (d-spacings) and typical relative intensities ($I/I_1$) are reported.

U.S. Pat. No. 5,703,232 (hereinafter "the '232 patent") claims lower alcohol solvates of olanzapine referred to in the '232 patent as "Form I" and methods for their preparation. The polymorph designated as "Form I" in the '232 patent has the same characteristic interplanar spacing by X-ray diffraction as "Form II" of the '541 patent and should thus be considered the same polymorph. Similarly, the polymorph designated as "Form II" in the '232 patent has the same characteristic interplanar spacing by X-ray diffraction as the polymorph designated as "Form I" in the '541 patent and should thus be considered the same polymorph. As used hereinafter the terms "Form I" and "Form II" refer to the olanzapine products designated as "Form I" and "Form II" in the '541 patent having the interplanar spacings and typical relative intensities shown in Table 1.

The present invention satisfies a need for additional stable, anhydrous and solvate-free polymorphic forms of olanzapine useful in the preparation of pharmaceutical formulations.

SUMMARY OF THE INVENTION

The present invention provides new polymorphic forms of 2-methyl-4-[4-methyl-1-piperazinyl]-10H-thieno[2,3b][1,5] benzodiazepine (olanzapine) designated as "Form III", "Form IV" and "Form V", methods of preparing the new polymorphic forms of olanzapine and pharmaceutical compositions containing them.

The invention produces new substantially pure polymorphs of olanzapine in high yield. The invention further differs from the prior art by requiring only aqueous solvents to prepare the stable polymorphs. The invention also provides an advantage over the prior art by isolating the new olanzapine polymorphs in a solvent free media, thus producing olanzapine free of solvates and having a negligible solvent content.

The invention provides three novel, solvate free forms of olanzapine designated Form III, Form IV and Form V. The novel forms of olanzapine are characterized by their unique x-ray diffraction patterns and infrared spectra.

The invention further provides a process for preparing the novel forms of olanzapine by first dissolving olanzapine in an aqueous organic or inorganic acid, which may be acetic acid, formic acid, hydrochloric acid, sulfuric acid, citric acid, fumaric acid or maleic acid. Hydrochloric acid, sulfuric acid, formic acid and acetic acid are exemplary acids. The new form of olanzapine is then precipitated using an aqueous or alcoholic solution of alkali, which may be potassium hydroxide, sodium hydroxide or ammonia. The alcoholic solvent may be any mono, di, or polyhydric alcohol, such as, for example, methanol. The olanzapines obtained typically contain less than 5% of other forms of olanzapine and less than 1% of other impurities. The desired form of olanzapine can be obtained by varying the acid or its concentration, and the temperature and pH of precipitation. The acid solution used in preparing the novel forms of olanzapine may contain between about 5% and about 50% acid. Olanzapine is precipitated at a temperature between, for example, about 0° C. and about 100° C., between about 0° C. and about 35° C. or between about 10° C. and about 30° C. The final pH of the solution, after precipitation, is, for example, between about 6 and about 12, or between about 8 and about 11.

The invention also provides pharmaceutical formulations containing as an active ingredient at least one of Form III olanzapine, Form IV olanzapine, Form V olanzapine or a pharmaceutically acceptable salt thereof. Pharmaceutical compositions may further contain one or more pharmaceutically acceptable carriers, excipients or diluents.

The invention further provides a method of treating a psychotic condition, mild anxiety or gastrointestinal conditions by administering an effective amount of at least one of Form III, Form IV or Form V olanzapine or a pharmaceutically acceptable salt thereof to a patient. The invention further provides a method of treating a a patient having a psychotic condition selected from schizophrenia and related disorders, acute mania, Bipolar I Disorder, psychotic mood disorder and psychosis with Alzheimer's disease by administering an effective amount of at least one of Form III, Form IV or Form V olanzapine or a pharmaceutically acceptable salt thereof to a patient having such a condition.

The above objectives and advantages of the invention are illustrative, and not exhaustive, of those which can be achieved by the invention and the examples presented herein are non-limiting. Thus, these and other objectives and advantages of the invention will be apparent from the description herein, both as embodied herein and as modified in view of any variations which will be apparent to those skilled in the art.

BRIEF DESCRIPTION OF THE DRAWINGS

Embodiments of the invention are explained in greater detail by way of the accompanying figures.

DETAILED DESCRIPTION OF THE INVENTION

The process of the present invention consists of dissolving olanzapine in aqueous acid and precipitating olanzapine from the resultant salt solution using an aqueous or alcoholic solution of alkali. Alcoholic solutions include any mono-, di- or polyhydric alcohol. A methanolic solution is a particular example. The acids to be used in the present invention may be any suitable organic or inorganic acid, for example, hydrochloric acid, sulfuric acid, acetic acid, formic acid, citric acid, fumaric acid, and maleic acid. Hydrochloric acid, sulfuric acid, acetic acid and formic acid are exemplary acids. The concentration of acid may range from 5% to 50%.

Either Form I or Form II olanzapine may be used as a starting material in the invention. The preferred olanzapine used in preparing the novel polymorphs of the invention is Form I olanzapine obtained by the method described in U.S. Pat. No. 5,229,382, which is herein incorporated by reference in its entirety.

The Form I or Form II olanzapine is mixed with the selected acid and stirred at a suitable temperature until dissolved completely. The solution is then neutralized using a base selected from aqueous or alcoholic sodium hydroxide, aqueous or alcoholic potassium hydroxide or aqueous ammonia. The alcohol solvent may be any mono, di, or polyhydric alcohol. Methanol is an example of an alcoholic solvent.

The temperature of precipitation is between about 0° C. and about 100° C., or between about 0° C. and about 35° C. or between about 10° C. and about 30° C. During precipitation, the pH of the precipitate is adjusted to be between about 6 and about 12, or between about 8 and about 11. The novel polymorphs of the invention are obtained in substantially pure form. The term "substantially pure" as used herein means that the polymorphs contain less than 5% of other forms of olanzapine and less than 1% of other impurities, water or solvates.

Figure 3:
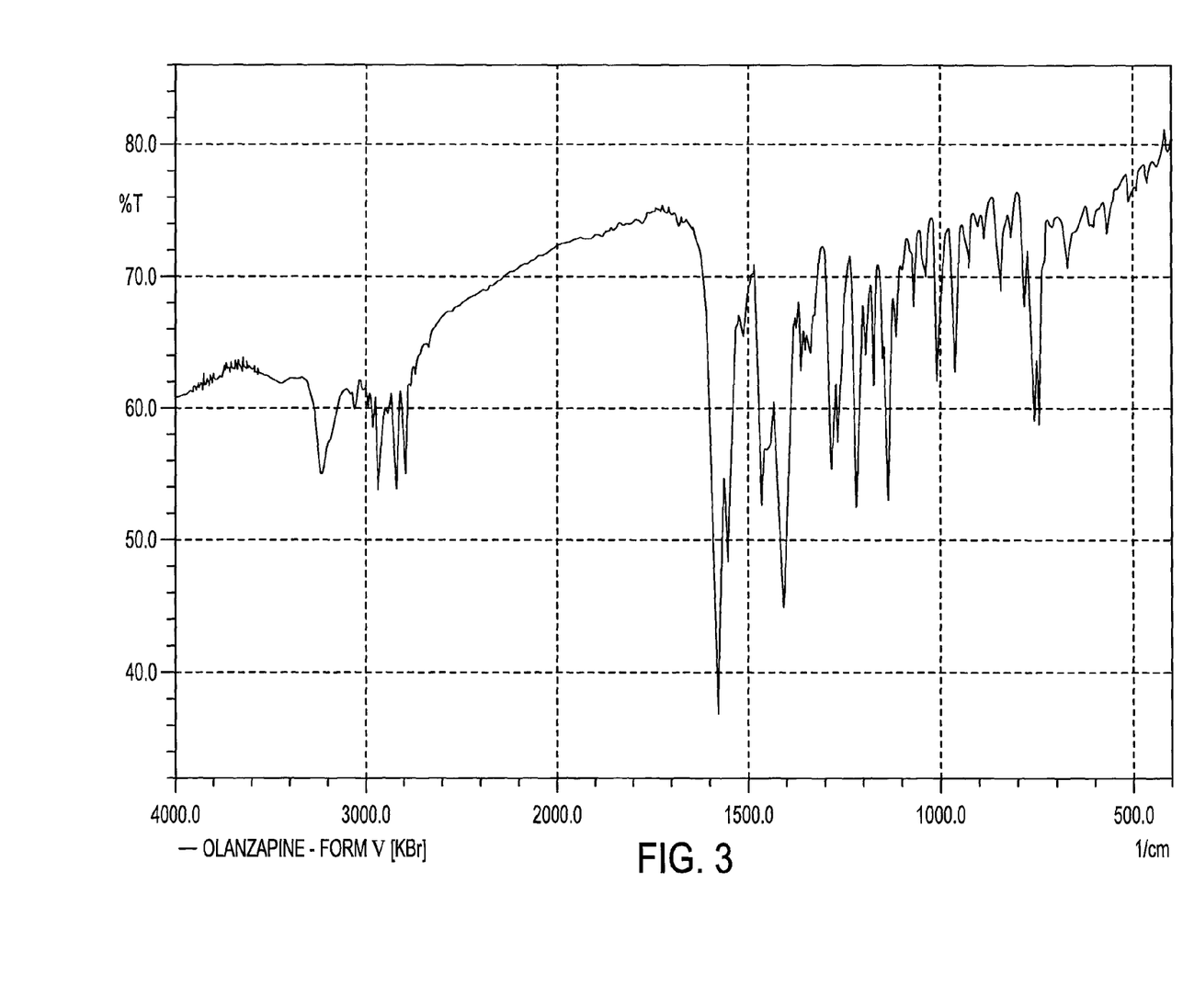
FIG. 3 is a FT-IR spectrum of Form V olanzapine.
Figure 4:
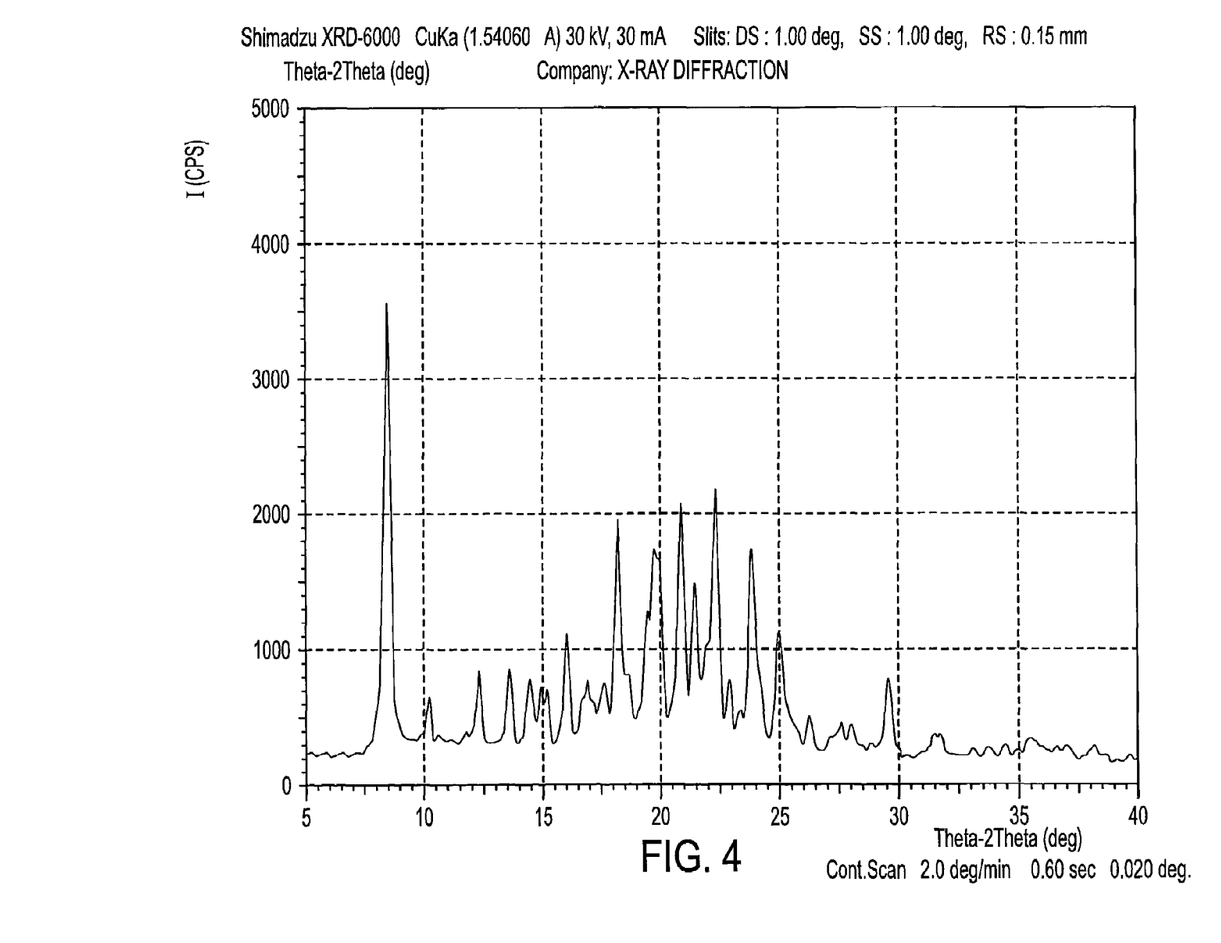
FIG. 4 is the X-ray diffraction pattern obtained for Form III olanzapine.
Figure 5:
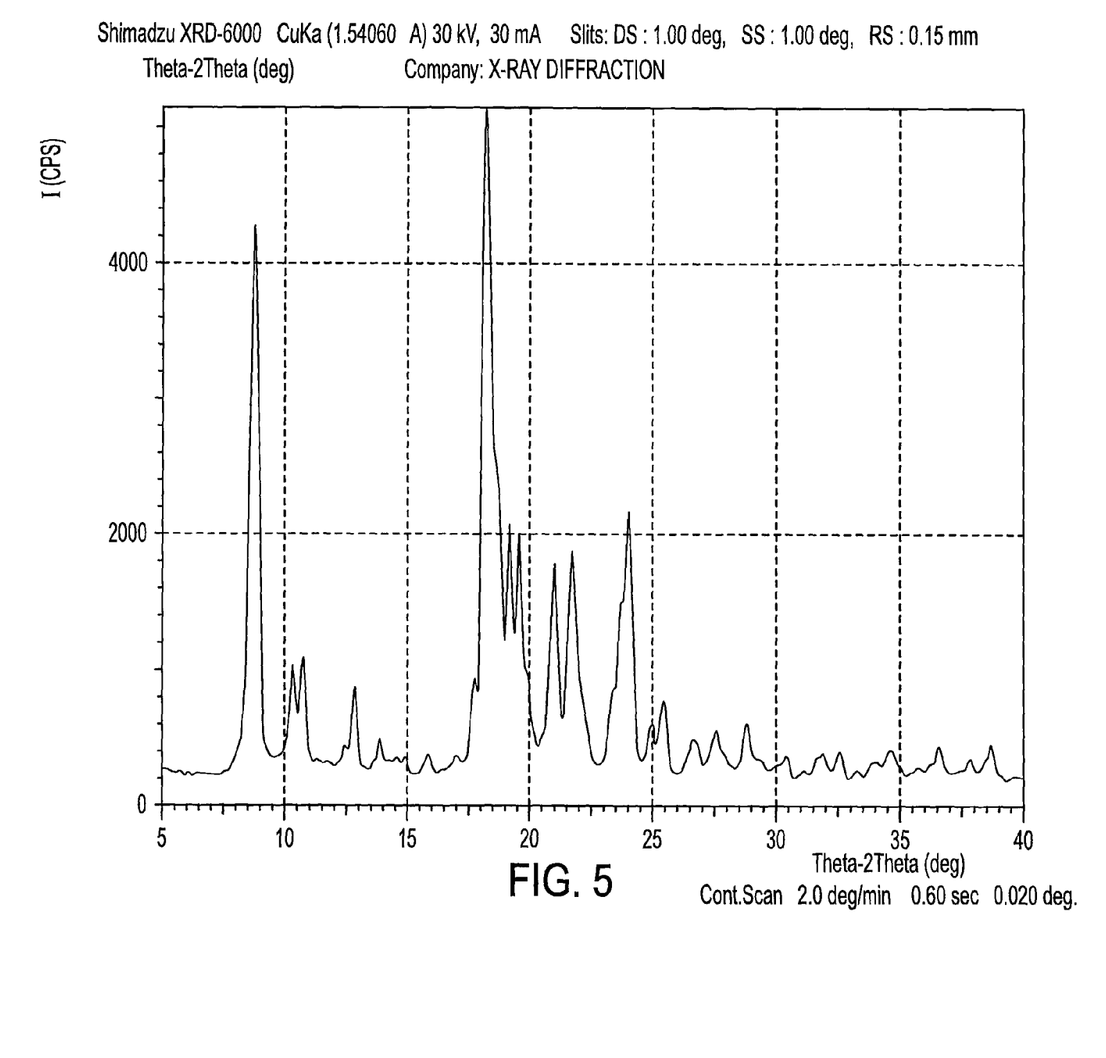
FIG. 5 is the X-ray diffraction pattern obtained for Form IV olanzapine.
Figure 6:
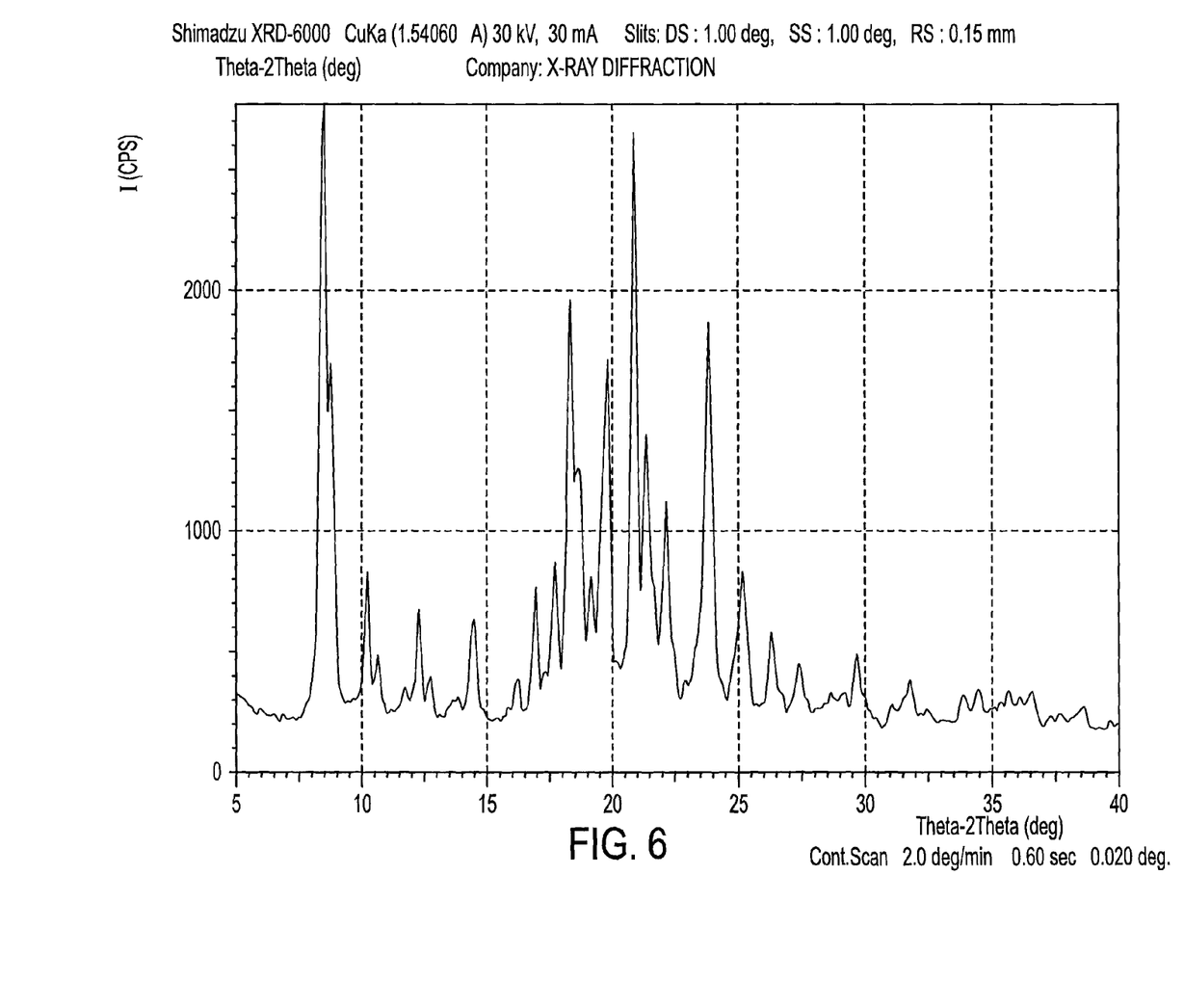
FIG. 6 is the X-ray diffraction pattern obtained for Form V olanzapine.

The novel polymorphs of the invention have been characterized by powder x-ray diffraction (XRD) patterns obtained using a Shimadzu X-ray diffractometer XRD-6000, equipped with a wide range goniometer and using copper Kα radiation as set forth in FIGS. 4–6. The interplanar spacings (in Angstroms) and typical relative intensities (I/I$_1$) sufficient to identify Forms III, IV, and V olanzapine according to the invention are set forth in Table 3. The complete set of interplanar spacings and relative intensities for Forms III, IV, and V olanzapine are set forth in Table 5. The novel polymorphs were further characterized by infrared (IR) spectroscopy obtained in a KBr disk using a Shimadzu FT-IR 8201 PC system as set forth in FIGS. 1–3. The IR absorbances (in wavenumbers, cm$^{-1}$) sufficient to identify Forms III, IV, and V olanzapine are set forth in Table 2. The complete set of IR absorbances for Forms III, IV, and V olanzapine are set forth in Table 4.

Form III olanzapine may be prepared by dissolving Form I or Form II olanzapine in about 50% aqueous acetic acid and precipitating the compound using about 15% aqueous ammonia to a final pH of about 8. Alternatively, Form III olanzapine may be obtained by dissolving Form I or Form II olanzapine in about 33% aqueous acetic acid and precipitating the compound using about 50% aqueous sodium hydroxide to a pH of about 10. Form III olanzapine is characterized by the infrared (IR) spectrum of FIG. 1 and by the X-ray diffraction pattern (XRD) of FIG. 4. The IR absorbances and XRD peaks sufficient to identify Form III olanzapine are contained in Tables 2 and 3, respectively. The complete set of IR absorbances and XRD peaks for Form III olanzapine are provided in Tables 4 and 5, respectively.

Form IV olanzapine may be prepared by dissolving Form I or Form II olanzapine in about 38% aqueous formic acid and precipitating the compound using about 10% methanolic sodium hydroxide to a final pH of about 8. Alternatively, Form IV olanzapine may be prepared by dissolving Form I or Form II olanzapine in about 43% aqueous acetic acid and precipitating the compound using about 25% ammonia to a final pH of about 10. Form IV olanzapine is characterized by the IR spectrum of FIG. 2 and by the XRD of FIG. 5. The IR absorbances and XRD peaks sufficient to identify Form IV olanzapine are contained in Tables 2 and 3, respectively. The complete set of IR absorbances and XRD peaks for Form IV olanzapine are provided in Tables 4 and 5, respectively.

Form V olanzapine may be prepared by dissolving Form I or Form II olanzapine in about 10% aqueous hydrochloric acid and precipitating the compound using about 10% aqueous sodium hydroxide to a final pH of about 8.5. Alternatively, Form V olanzapine may be prepared by dissolving Form I or Form II olanzapine in about 40% aqueous acetic acid and precipitating the compound using about 50% aqueous sodium hydroxide to a final pH of about 9. Form V olanzapine may also be obtained by dissolving Form I or Form II olanzapine in about 20% formic acid and precipitating the compound using about 25% aqueous ammonia. Also, Form V olanzapine may be prepared by dissolving Form I or Form II olanzapine in about 50% acetic acid and precipitating the compound using about 25% ammonia to a final pH of about 9. Form V olanzapine is characterized by the IR spectrum of FIG. 3 and by the XRD of FIG. 6. The IR absorbances and XRD peaks sufficient to identify Form V olanzapine are contained in Tables 2 and 3, respectively. The complete set of IR absorbances and XRD peaks for Form V olanzapine are provided in Tables 4 and 5, respectively.

The methods of the invention may be used for the purification of olanzapine, as well as for preparation of the new polymorphic forms. For example, 97% pure (by HPLC) Form I olanzapine may be converted to approximately 99% pure Form III olanzapine (HPLC) by dissolving olanzapine in about 33% aqueous acetic acid and precipitating Form III olanzapine using about 50% aqueous sodium hydroxide to a final pH of about 10.

Olanzapine, like clozapine, is classified as an atypical antipsychotic drug. Olanzapine interacts with key receptors of interest in schizophrenia and has a nanomolar affinity for dopaminic, serotonergic, $\alpha_1$-adrenergic and muscarinic receptors. (See, for example, F P Bymaster et al. *J. Clin. Psychiatry,* 1997; Vol. 58 (suppl 10): 28–36, which is incorporated herein by reference in its entirety.) Olanzapine shows relatively non-selective binding with dopamine receptors ($D_1$ to $D_5$). Olanzapine also interacts with several types of serotonin (5-HT) receptors and is a potent inhibitor of $5\text{-HT}_{2A}$, $5\text{-HT}_{2B}$, $5\text{-HT}_{2C}$, and $5\text{-HT}_6$ receptors. Olanzapine is also a potent inhibitor of all five subtypes of the muscarinic cholinergic receptor and $\alpha$-adrenergic receptor. In addition, olanzapine shows mesolimbic and mesocortical selectivity.

The olanzapine polymorphs described herein may be used in the same manner as other olanzapine polymorphs. For example, olanzapine polymorphs of the invention may be used therapeutically and for the preparation of pharmaceutical compositions.

Olanzapine has been found to have a wide range of therapeutic effects, particularly for the treatment of schizophrenia, schizophreniform disorders, psychosis, mild anxiety states and functional bowel disorders. The various disorders which may be treated using olanzapine are described in detail in the '541 patent at column 4, line 62 through column 8, line 55.

The use and efficacy of olanzapine in the treatment of schizophrenia, bipolar disorder and related disorders has been extensively studied and demonstrated. (See for example, Schizophrenia—J C Gomez and A M K Crawford *J. Clin. Psychiatry* 2001; Vol. 62 (suppl 2): 6–11; K H Littrell et al. *J. Clin. Psychiatry* 2000, Vol. 61: 912–915; P V Tran et al. *J. Clin. Psychiatry* 1997 Vol. 17: 407–417; J C Kando, et al. *Annals of Pharmacotherapy* 1997 Vol. 31: 1325–34; C B Nemeroff *J. Clin. Psychiatry* 1997; 58 (suppl 10): 45–49; C M Beasley *J. Clin. Psychiatry* 1997; Vol. 58 (suppl 10): 7–12; Bipolar Disorder—C Guille et al. *J. Clin. Psychiatry* 2000 Vol. 61: 638–642; each of which is incorporated by reference herein in its entirety.) The long term use of olanzapine has been shown to be effective and promising in some patient groups and has been suggested for long term monotherapy and adjuvant therapy. This is particularly true for patients having schizophrenia and psychotic mood disorders. (See R Narendran *J. Clin. Psychiatry* 2001, Vol. 62: 509–516, which is incorporated by reference herein in its entirety)

For example, Narendran, in discussing the use of olanzapine to treat psychotic mood disorders cites that "preliminary data on olanzapine in patients with schizophrenia, schizophreniform disorder, and schizoaffective disorders suggested that his drug may posses acute antimanic and antidepressant properties in addition to its antipsychotic proprieties." Several studies indicating the efficacy of olanzapine were described:

Baker et al. reported that patients with schizophrenia treated with 10 mg/day of olanzapine were noted to have a significant reduction in Hamilton Rating Scale for Depression scores in comparison with those receiving olanzapine, 1 mg/day, or placebo. Tollefson et al. examined the efficacy of olanzapine in treating depressive signs and symptoms associated with schizophrenia and schizoaffecive and schizophreniform disorders in a 6-week double-blind, placebo-controlled trial. Olanzapine was found to be statistically superior to haloperidol in baseline to endpoint changes as measured by the Montgomery-Asberg Depression Rating Scale (MADRS) total score (6-point decline compared with a 3-point decline with haloperidol, p=0.001). The authors concluded that olanzapine had a direct therapeutic effect on the depressive signs and symptoms after covarying for indirect effects, including positive, negative, and extrapyramidal symptoms via a linear regression "path analysis." For that trial, a recent subanalysis of schizoaffective disorder, bipolar type patients was reported. In the schizoaffective patients who were currently depressed, olanzapine was noted to be superior to haloperidol in the reduction of the MADRS scores (p=0.002). In the schizoaffective patients who were currently manic, olanzapine was as effective as haloperidol in decreasing the Brief Psychiatric Rating Scale (BPRS) mania score (p=0.25). (The BPRS mania score was derived by adding the BPRS items assessing conceptual disorganization, grandiosity, hostility, excitement, and disorientation.) In a retrospective naturalistic study of 150 consecutively admitted inpatients with a diagnosis of psychotic disorders treated with olanzapine, Zarate et al. reported an overall response rate of 62% for all patients and a statistically significant better response rate of 83% for the bipolar disorder patients. In a blinded chart review study of the treatment of 30 inpatients with psychotic depression. Rothschild and colleagues reported a response rate of 67% among patients treated with olanzapine compared with 27% in age- and sex-matched patients treated with typical antipsychotics.

(Narendran *J. Clin. Psychiatry* 2001 at 510: internal references omitted). In the original study conducted by Narendran by reviewing hospital records and by follow-up interviews, Narendran concluded:

Both the psychotic mood disorders patients (N=32) and the schizophrenic patients (N=18) who continued to be treated with olanzapine showed a statistically significant change toward improvement on the CGI and GAF-EQ during the course of this study (Table 3). Although the psychotic mood disorders cohort exhibited a greater change from baseline to follow-up on the CGI compared with the schizophrenic cohort, this difference between groups failed to reach statistical significance. Seventy-five percent (24/32) of the psychotic mood disorders patient group and 100% (18/18) of the schizophrenic patients taking olanzapine remained hospitalized at follow-up.

A subanalysis was performed on the individual subscale scores of the K Axis V before and after treatment with olanzapine after lowering the a value of significance utilizing the Bonferroni correction (Table 4). The psychotic mood disorders group revealed a statistically significant change from baseline to follow-up scores in the psychological impairment, violence, and social skills subscales in contrast to the schizophrenic group, which revealed a significant change in score only on the violence subscale.

Id. At 512.

Guille also conducted a review of medical records in patients with bipolar disorder who received at least one dose of olanzapine. The mean dosage was 11.7±6.2 mg/day. Guille found that in a 49-week open-label extension of a clinical trial of olanzapine for acute mania, 113 bipolar type I patients were followed for an average of 6.7 months while taking a mean dose of 13.8 mg/day of olanzapine. YMRS scores improved from 25.5 at baseline to 7.5 on follow-up (p<0.001), and HAM-D scores improved from 12.2 to 6.5 (p<0.001). Few EPS were noted. Adjunctive lithium was allowed, although the available abstract is unclear about how many patients received lithium.

Guille et al. *J. Clin. Psychiatry* 2000 at 640.

Olanzapine has also been shown to be an effective therapy for the treatment of psychosis among patients with Alzheimer's disease (AD). (W S Clark *J. Clin. Psychiatry* 2001; Vol. 62: 34–40, which is incorporated by reference herein in its entirety, and references cited therein.) This study shows that, in patients with possible AD with concurrent agitation/aggression and no or minimal hallucinations and/or delusions, olanzapine treatment results in an overall significantly lower emergence of psychotic symptoms compared to placebo. For example, Clark studied a group of nursing home patients and found that:

The results of these post hoc analyses indicate that, overall, olanzapine was effective in decreasing the emergence of psychotic symptoms in patients with AD who were relatively free of these symptoms at baseline. Previous studies have demonstrated that olanzapine is effective in reducing psychotic symptoms in schizophrenia, acute mania, and AD. Moreover, in a recent report. olanzapine was shown to prevent relapse of psychosis in stable schizophrenic patients. suggesting it may have a prophylactic effect as well as an ameliorative effect on psychosis. This is study is the first to suggest that olanzapine may effectively attenuate the emergence of acute psychosis in patients with AD.

The effect pattern seen here for the 3 doses of olanzapine was not consistent with the efficacy results in the overall study. The parent study found the 5-mg/day dose to be not only the most efficacious in reducing psychotic symptoms but also the safest. The 10-mg/day dose also demonstrated significant efficacy for olanzapine relative to placebo, but the results were less rebust. The 15-mg/day dose group failed to separate from the placebo group in their expression of psychotic symptoms and had a less tolerated safety profile. In contrast, the results here indicate attenuation of the emergence of psychosis across the 3 olanzapine doses, with a tendency toward greater effects at the higher doses. The sample size and short duration of this study are limitations that do not allow powerful comparisons among olanzapine doses. Given the safety and efficacy results from the parent study in combination with the findings here, 5 mg/day of olanzapine would be the most appropriate target does for further study on reducing the emergence of psychosis in dementia.

Clark *J. Clin. Psychiatry* 2001 at 38–39.

Further, olanzapine has demonstrated efficacy in patients with Acute Mania. (M Tohen *Am. J. Psychiatry* 1999 Vol. 156: 702–709, which is incorporated by reference herein in its entirety.) Tohen conducted a randomized, placebo-controlled, double-blind study of pateients between 18 and 65 years of age. Dosages were in the range of 5–20 mg/day, adjust individually after an initial treatment with 10 mg/day. Tohen found:

This suggests that olanzapine is effective in the treatment of acute mania, as evidenced by the decreases in total scores on the Young Mania Rating Scale; in severity of mania ratings on the CGI, Bipolar Version; and in total and positive symptom scores on the Positive and Negative Syndrome Scale. Also, the percentage of patients who discontinued treatment because of lack of efficacy was significantly smaller (p=0.02) in the olanzapine group (28.6%) than in the placebo group (47.8%). That olanzapine may have antimaine effects is further suggested by the magnitude of response to treatment as illustrated by the responder analysis, where 48.6% of the olanzapine-treated patients had an improvement of 50% or more in Young Mania Rating Scale total score, compared with 24.2% of the placebo-treated patients.

Tohen *Am. J. Psychiatry* 1999 at 706.

Pharmaceutical formulations according to the invention comprise Form III, IV or V olanzapine or a pharmaceutically acceptable salt thereof as an active ingredient together with one or more pharmaceutically acceptable carriers, excipients or diluents. Any conventional technique may be used for the preparation of pharmaceutical formulations according to the invention. The active ingredient may be contained in a formulation that provides quick release, sustained release or delayed release after administration to the patient.

Pharmaceutical compositions that are useful in the methods of the invention may be prepared, packaged, or sold in formulations suitable for oral, parenteral and topical administration. Other contemplated formulations include nanoparticles, liposomal preparations, resealed erythrocytes containing the active ingredient, and immunologically-based formulations.

The formulations of the pharmaceutical compositions described herein may be prepared by any method known or hereafter developed. In general, preparation includes bringing the active ingredient into association with a carrier or one or more other additional components, and then, if necessary or desirable, shaping or packaging the product into a desired single- or multi-dose unit.

As used herein, "additional components" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; pharmaceutically acceptable polymeric or hydrophobic materials as well as other components.

Although the descriptions of pharmaceutical compositions provided herein are principally directed to pharmaceutical compositions which are suitable for administration to humans, it will be understood by the skilled artisan, based on this disclosure, that such compositions are generally suitable for administration to any mammal. Preparation of compositions suitable for administration to various animals is well understood, and the ordinarily skilled veterinary pharmacologist can design and perform such modifications with routine experimentation based on pharmaceutical compositions for administration to humans.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient in each unit dose is generally equal to the total amount of the active ingredient which would be administered or a convenient fraction of a total dosage amount such as, for example, one-half or one-third of such a dosage.

A formulation of a pharmaceutical composition of the invention suitable for oral administration may in the form of a discrete solid dosage unit. Solid dosage units include, for example, a tablet, a caplet, a hard or soft capsule, a cachet, a troche, or a lozenge. Each solid dosage unit contains a predetermined amount of the active ingredient, for example a unit dose or fraction thereof. Other formulations suitable for administration include, but are not limited to, a powdered or granular formulation, an aqueous or oily suspension, an aqueous or oily solution, or an emulsion. As used herein, an "oily" liquid is one which comprises a carbon or silicon based liquid thatis less polar than water.

A tablet comprising the active ingredient may be made, for example, by compressing or molding the active ingredient, optionally containing one or more additional components. Compressed tablets may be prepared by compressing, in a suitable device, the active ingredient in a free-flowing form such as a powder or granular preparation, optionally mixed with one or more of a binder, a lubricant, a glidant, an excipient, a surface active agent, and a dispersing agent. Molded tablets may be made by molding, in a suitable device, a mixture of the active ingredient, a pharmaceutically acceptable carrier, and at least sufficient liquid to moisten the mixture.

Tablets may be non-coated or they may be coated using methods known in the art or methods to be developed. Coated tablets may be formulated for delayed disintegration in the gastrointestinal tract of a subject, for example, by use of an enteric coating, thereby providing sustained release and absorption of the active ingredient. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional components including, for example, an inert solid diluent. Soft gelatin capsules comprising the active ingredient may be made using a physiologically degradable composition, such as gelatin. Such soft capsules comprise the active ingredient, which may be mixed with water or an oil medium.

Liquid formulations of a pharmaceutical composition of the invention which are suitable for administration may be prepared, packaged, and sold either in liquid form or in the form of a dry product intended for reconstitution with water or another suitable vehicle prior to use.

Liquid suspensions, in which the active ingredient is dispersed in an aqueous or oily vehicle, and liquid solutions, in which the active ingredient is dissolved in an aqueous or oily vehicle, may be prepared using conventional methods or methods to be developed. Liquid suspension of the active ingredient may be in an aqueous or oily vehicle and may further include one or more additional components such as, for example, suspending agents, dispersing or wetting agents, emulsifying agents, demulcents, preservatives, buffers, salts, flavorings, coloring agents, and sweetening agents. Oily suspensions may further comprise a thickening agent. Liquid solutions of the active ingredient may be in an aqueous or oily vehicle and may further include one or more additional components such as, for example, preservatives, buffers, salts, flavorings, coloring agents, and sweetening agents.

Powdered and granular formulations according to the invention may be prepared using known methods or methods to be developed. Such formulations may be administered directly to a subject, or used, for example, to form tablets, to fill capsules, or to prepare an aqueous or oily suspension or solution by addition of an aqueous or oily vehicle thereto. Powdered or granular formulations may further comprise one or more of a dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. Such compositions may further comprise one or more emulsifying agents. These emulsions may also contain additional components including, for example, sweetening or flavoring agents.

Pharmaceutical compositions according to the present invention may contain, for example, 0.25 to 100 mg of active ingredient or 1 to 30 mg active ingredient, along with a pharmaceutically acceptable carrier.

Methods

Figure 1:
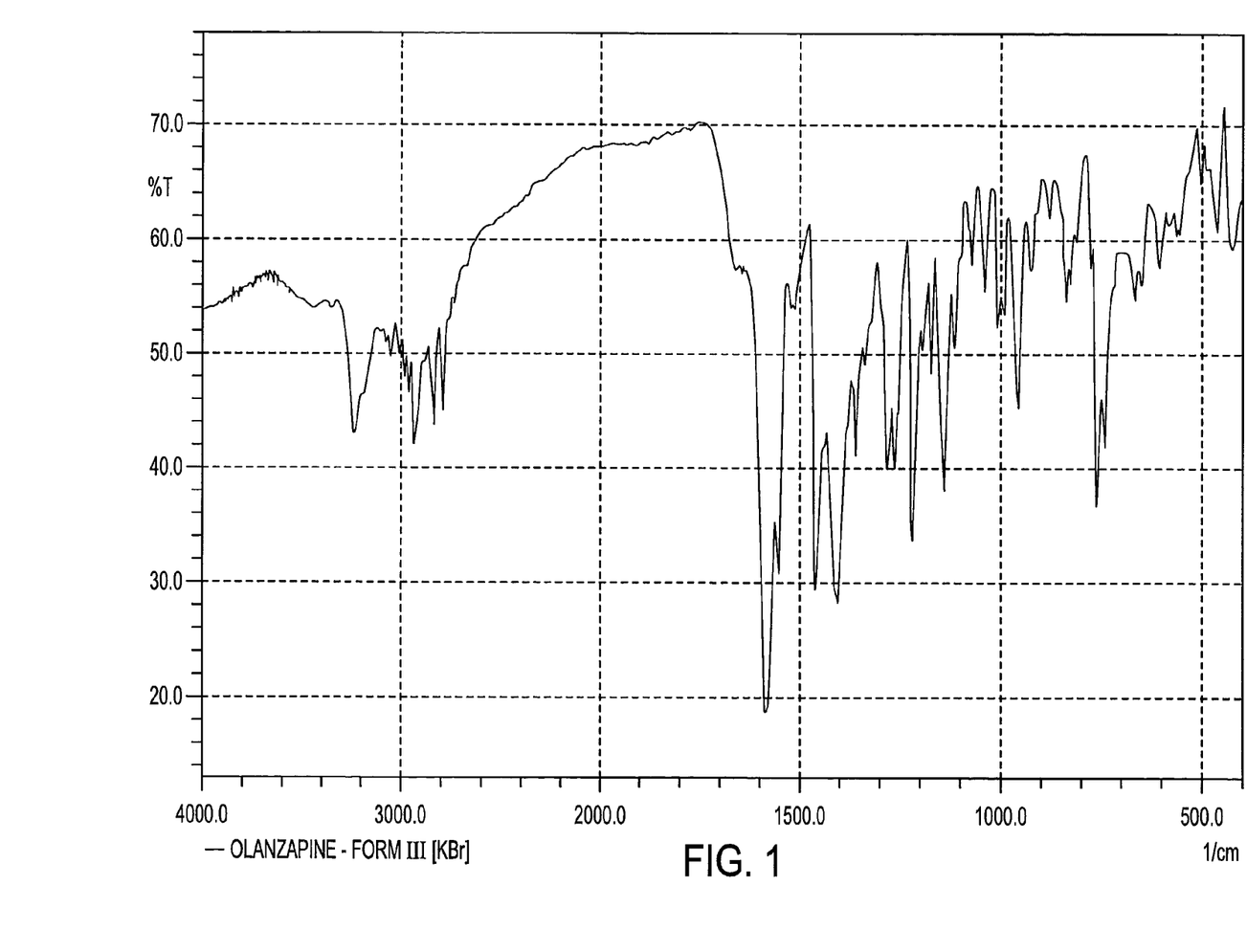
FIG. 1 is a FT-IR spectrum of Form III olanzapine.
Figure 2:
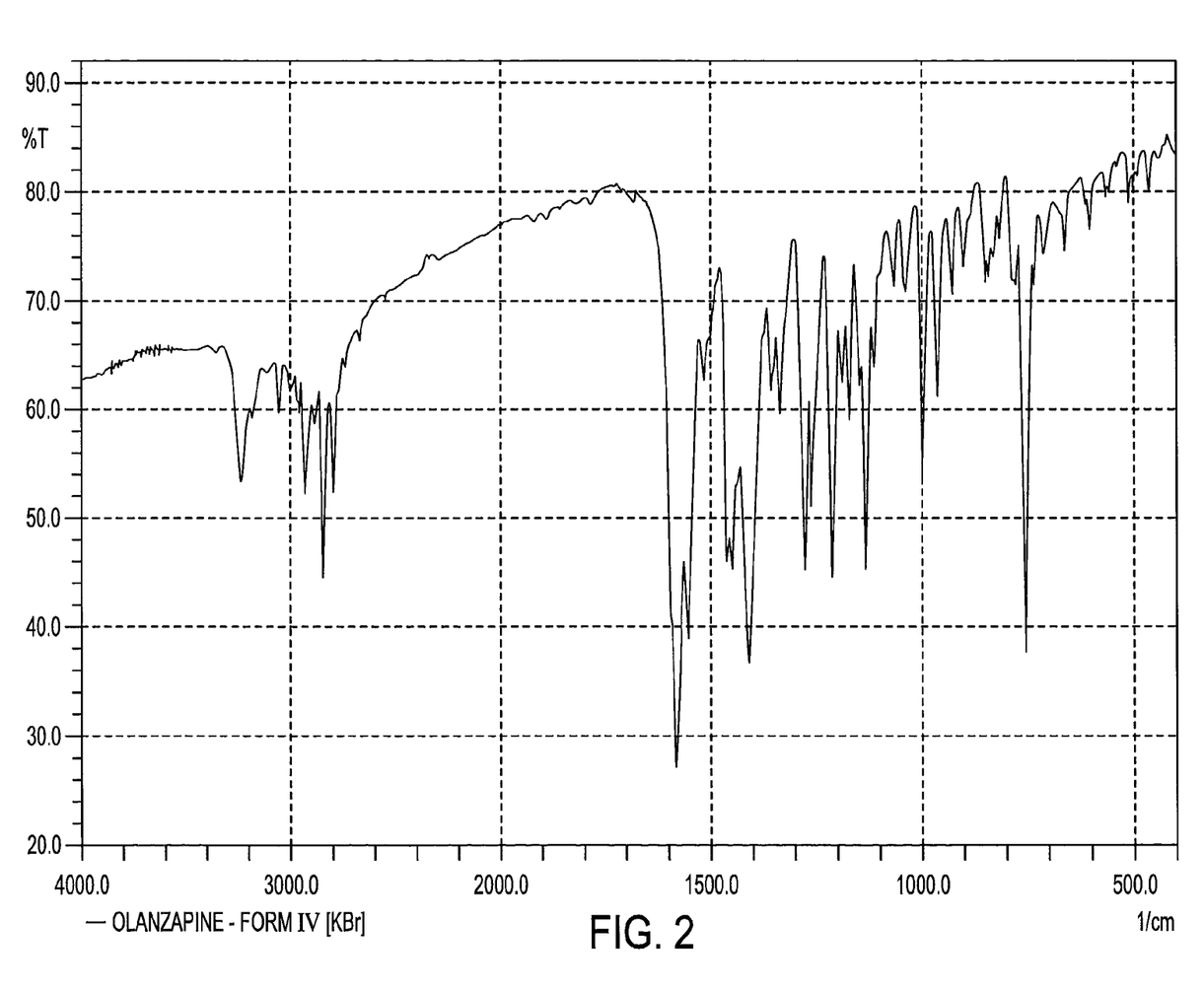
FIG. 2 is a FT-IR spectrum of Form IV olanzapine.

Form I olanzapine used as a starting material was obtained by the method described in U.S. Pat. No. 5,229,382. IR-Spectra were obtained in a KBr disk using a Shimadzu FT-IR 8201 PC system. The IR-Spectra obtained for the three polymorphic forms, i.e. Forms III, IV, and V, are shown in FIGS. 1, 2 and 3, respectively. A summary of wavenumbers sufficient to identify Forms III, IV and V olanzapine is provided in Table 2. Table 4 contains a complete listing of IR absorbances for Forms III, IV and V olanzapine according to the invention. Powder x-ray diffraction patterns were obtained on a Shimadzu X-ray diffractometer XRD-6000, equipped with a wide range goniometer using copper K$\alpha$ radiation. The powder x-ray diffraction patterns for the three polymorphic forms, i.e. Forms III, IV, and V, are provided in FIGS. 4, 5 and 6, respectively. The interplanar d-spacings sufficient to identify Forms III, IV and V olanzapine and their relative intensities are set forth in Table 3. The complete set of interplanar d-spacings and relative intensities for Forms III, IV and V olanzapine are provided in Table 5.

EXAMPLE 1

Form I olanzapine (10 g) was dissolved in a mixture of 30 ml acetic acid and 30 ml water by stirring. Activated charcoal (0.5 g) was added and the contents filtered over celite. The clear solution was maintained at 20° C. and 15% aqueous ammonia solution was added over a period of 30 minutes to adjust the pH to 8. The contents were filtered and dried to obtain Form III olanzapine (9.6 g), which was characterized by IR and XRD.

EXAMPLE 2

Form I olanzapine (10 g) was dissolved in a mixture of 30 ml acetic acid and 40 ml water and the contents filtered over celite. The clear solution was maintained at 20° C. and 30 ml of 25% aqueous ammonia solution was added rapidly in 10 minutes to adjust the pH to about 6. The solids precipitated slowly and the solution was stirred for 30 minutes. A further 30 ml of ammonia solution was added to the mass to obtain a pH of about 10. The contents were further stirred for 1 hour and filtered and dried to obtain Form IV olanzapine (9.4 g), which was charcterized by IR and XRD.

EXAMPLE 3

Form I olanzapine (10 g) was dislolved in a mixture of 40 ml acetic acid and 60 ml water and the contents filtered over celite. The clear solution was maintained at 20° C. and 50 ml of 50% aqueous sodium hydroxide solution was added rapidly with stirring to obtain a gummy mass. On stirring for a further 30 minutes, a fine suspension was obtained. The pH of the contents was adjusted to about 9 using additional sodium hydroxide solution. The product was recovered by filtration and dried to obain Form V olanzapine (9.4 g), which was characterized by IR and XRD.

EXAMPLE 4

Form I olanzapine (10 g) was dissolved in a mixture of 25 ml formic acid and 40 ml water by stirring. Activated charcoal (0.5 g) was added and the contents were filtered over celite. The clear solution was maintained at 10 to 15° C. and neutralized with 10% methanolic sodium hydroxide solution to a pH of 8. The product was recovered by filtration and dried to obtain Form IV olanzapine (9.3 g), which was characterized by IR and XRD.

EXAMPLE 5

Form I olanzapine (10 g) was dissolved in a mixture of 10 ml formic acid and 40 ml water and the solution was filtered over celite. This solution was added slowly to a stirred 25% aqueous ammonia solution (70 ml) to which a few seed crystals of Form V olanzapine were added. The temperature was maintained between 15 to 25° C. during the addition. The contents were stirred for 1 hour and filtered and dried to obtain Form V olanzapine (9.4 g), which was characterized by IR and XRD.

EXAMPLE 6

Form I olanzapine (10 g) obtained by the method described in U.S. Pat. No. 5,229,352 and having a purity of 97% (HPLC) was dissolved in a mixture of 30 ml acetic acid and 60 ml water and the solution filtered over celite. The solution was maintained at 20° C. with stirring and 50% aqueous sodium hydroxide solution added to adjust the pH to between 6 and 6.2. The solids which precipitated were stirred for 45 minutes and filtered. The wet cake was taken up in water (50 ml) and additional sodium hydroxide added to adjust the pH to 10. The contents were stirred for 1 hour and filtered. The product was dried to obtain >99% pure Form III olanzapine (9.1 g), which was characterized by IR and XRD.

EXAMPLE 7

Form I olanzapine (10 g) was dissolved in 50 ml of 10% hydrochloric acid with stirring. Activated charcoal (0.5 g) was added and the contents filtered over celite. The clear solution was maintained at 15° C. and neutralized to a pH of 8.5 with 10% aqueous sodium hydroxide solution. The product was recovered by filtration and dried to obtain Form V olanzapine (9.5 g), which was characterized by IR and XRD.

EXAMPLE 8

Form I olanzapine (10 g) was dissolved in a mixture of 30 ml acetic acid and 30 ml water and the contents filtered over celite. This solution was added to 60 ml of a stirred 25% aqueous ammonia solution seeded with a few crystals of Form V olanzapine. The temperature was maintained at 15 to 25° C. during the addition of the Form I solution to the aqueous ammonia solution and the pH of the mass was 9 after completion of the addition. After stirring for 1 hour, the product was recovered by filtration and dried to obtain Form V olanzapine which was characterized by IR and XRD.

Certain representative embodiments of the invention are described in the examples given above. The materials used and the process steps are intended as illustrative of the invention and the invention is not limited to the methods, process steps or any other conditions described in the examples. The examples are non-limiting and may be modified or varied, and elements added or omitted, without departing from the invention, as appreciated by those skilled in the art.

TABLE 1

X-RAY DIFFRACTION PEAKS OF FORM I AND FORM II OLANZAPINE SUMMARY OF d-spacing AND $I/I_1$ INTENSITY RATIO

| FORM I | | FORM II | |
| --- | --- | --- | --- |
| d-spacing | $I/I_1$ | d-spacing | $I/I_1$ |
| 9.9463 | 100.00 | 10.2689 | 100.00 |
| 8.5579 | 15.18 | 8.577 | 7.96 |
| 8.2445 | 1.96 | 7.4721 | 1.41 |
| 6.8862 | 14.73 | 7.125 | 6.50 |
| 6.3787 | 4.25 | 6.1459 | 3.12 |
| 6.2439 | 5.21 | 6.071 | 5.12 |
| 5.5895 | 1.10 | 5.4849 | 0.52 |
| 5.3055 | 0.95 | 5.2181 | 6.86 |
| 4.9815 | 6.14 | 5.1251 | 2.47 |
| 4.8333 | 68.37 | 4.9874 | 7.41 |
| 4.7255 | 21.88 | 4.7665 | 4.03 |
| 4.6286 | 3.82 | 4.7158 | 6.80 |
| 4.533 | 17.83 | 4.4787 | 14.72 |
| 4.4624 | 5.02 | 4.3307 | 1.48 |
| 4.2915 | 9.19 | 4.2294 | 23.19 |
| 4.2346 | 18.88 | 4.141 | 11.28 |
| 4.0855 | 17.29 | 3.9873 | 9.01 |
| 3.8254 | 6.49 | 3.7206 | 14.04 |
| 3.7489 | 10.64 | 3.5645 | 2.27 |
| 3.6983 | 14.65 | 3.5366 | 4.85 |
| 3.5817 | 3.04 | 3.3828 | 3.47 |
| 3.5064 | 9.23 | 3.2516 | 1.25 |
| 3.3392 | 4.67 | 3.134 | 0.81 |
| 3.2806 | 1.96 | 3.0848 | 0.45 |
| 3.2138 | 2.52 | 3.0638 | 1.34 |
| 3.1118 | 4.81 | 3.0111 | 3.51 |
| 3.0507 | 1.96 | 2.8739 | 0.79 |
| 2.948 | 2.40 | 2.8102 | 1.47 |
| 2.8172 | 2.89 | 2.7217 | 0.20 |
| 2.7589 | 2.27 | 2.6432 | 1.26 |
| 2.6597 | 1.86 | 2.6007 | 0.77 |
| 2.6336 | 1.10 | | |
| 2.5956 | 1.73 | | |

TABLE 2

FT-IR PEAKS OF FORM III, FORM IV AND FORM V OLANZAPINE SUMMARY OF WAVENUMBERS

| FORM-III $cm^{-1}$ | FORM-IV $cm^{-1}$ | FORM-V $cm^{-1}$ |
| --- | --- | --- |
| — | 604 | 604 |
| 611 | — | — |
| 656 | 661 | — |
| 671 | — | 671 |
| 746 | — | 746 |
| 765 | 758 | 758 |
| 845 | — | 847 |
| — | 904 | — |
| 935 | 931 | 928 |
| — | — | 1357 |
| 1369 | 1365 | 1369 |
| — | 1456 | — |

TABLE 3

X-RAY DIFFRACTION PEAKS OF FORM III, FORM IV AND FORM V OLANZAPINE SUMMARY OF d-spacing AND $I/I_1$ INTENSITY RATIO

| FORM-III | | | FORM-IV | | | FORM-V | | |
|---|---|---|---|---|---|---|---|---|
| 2-theta (deg.) | d-spacing | $I/I_1$ | 2-theta (deg.) | d-spacing | $I/I_1$ | 2-theta (deg.) | d-spacing | $I/I_1$ |
| 8.5649 | 10.3156 | 100 | 8.8814 | 9.9487 | 83 | 8.3400 | 10.5932 | 17 |
| 12.3325 | 7.1713 | 16 | 10.3898 | 8.5074 | 15 | 8.6477 | 10.2170 | 100 |
| 13.6091 | 6.5014 | 17 | 10.7669 | 8.2103 | 17 | 8.8800 | 9.9503 | 57 |
| 16.0535 | 5.5165 | 24 | 18.4029 | 4.8172 | 100 | 10.3673 | 8.5259 | 22 |
| 18.2617 | 4.8541 | 46 | 18.8200 | 4.7114 | 41 | 12.4540 | 7.1016 | 17 |
| 19.4600 | 4.5578 | 24 | 19.2284 | 4.6122 | 35 | 14.5737 | 6.0731 | 17 |
| 19.7400 | 4.4938 | 38 | 19.5884 | 4.5282 | 33 | 17.0243 | 5.2041 | 19 |
| 19.9200 | 4.4536 | 36 | 20.9646 | 4.2340 | 29 | 17.7763 | 4.9856 | 20 |
| 20.8409 | 4.2588 | 49 | 21.7109 | 4.0901 | 32 | 18.4102 | 4.8153 | 62 |
| 22.2635 | 3.9898 | 52 | 23.6600 | 3.7574 | 23 | 18.6600 | 4.7514 | 34 |
| 23.8442 | 3.7288 | 42 | 24.0400 | 3.6989 | 40 | 19.5800 | 4.5302 | 24 |
| 24.9738 | 3.5626 | 25 | | | | 19.8400 | 4.4714 | 51 |
| 29.4932 | 3.0262 | 18 | | | | 20.9993 | 4.2271 | 91 |
| | | | | | | 21.4949 | 4.1307 | 40 |
| | | | | | | 22.2738 | 3.9880 | 31 |
| | | | | | | 23.5400 | 3.7763 | 10 |
| | | | | | | 23.9232 | 3.7167 | 62 |
| | | | | | | 25.1975 | 3.5315 | 22 |

TABLE 4

COMPLETE FT-IR PEAKS OF FORM III, FORM IV AND FORM V OLANZAPINE SUMMARY OF WAVENUMBERS

| FORM-III $cm^{-1}$ | FORM-IV $cm^{-1}$ | FORM-V $cm^{-1}$ |
|---|---|---|
| — | 604 | 604 |
| 611 | — | — |
| 656 | 661 | — |
| 671 | — | 671 |
| 746 | — | 746 |
| 765 | 758 | 758 |
| 845 | — | 847 |
| — | 904 | — |
| 935 | 931 | 928 |
| 966 | 970 | 966 |
| 1008 | 1005 | 1006 |
| 1348 | 1344 | 1344 |
| — | — | 1357 |
| 1369 | 1365 | 1369 |
| 1414 | 1419 | 1414 |
| — | 1456 | 1414 |
| — | 1456 | — |
| 1469 | 1469 | 1469 |
| 1560 | 1560 | 1560 |
| 1593 | 1589 | 1585 |
| 2790 | 2798 | 2792 |
| 2837 | 2842 | 2839 |
| 2933 | 2927 | 2931 |
| 3232 | 3234 | 3228 |

TABLE 5

COMPLETE X-RAY DIFFRACTION PEAKS OF FORM III, FORM IV AND FORM V OLANZAPINE SUMMARY OF d-spacing AND $I/I_1$ INTENSITY RATIO

| FORM-III | | | FORM-IV | | | FORM-V | | |
|---|---|---|---|---|---|---|---|---|
| 2-theta (deg.) | d-spacing | $I/I_1$ | 2-theta (deg.) | d-spacing | $I/I_1$ | 2-theta (deg.) | d-spacing | $I/I_1$ |
| 8.22 | 10.7476 | 15 | 8.88 | 9.9487 | 83 | 8.34 | 10.5932 | 17 |
| 8.56 | 10.3156 | 100 | 10.39 | 8.5074 | 15 | 8.65 | 10.2170 | 100 |
| 10.25 | 8.6245 | 11 | 10.77 | 8.2103 | 17 | 8.88 | 9.9503 | 57 |
| 12.33 | 7.1713 | 16 | 12.88 | 6.8673 | 12 | 10.37 | 8.5259 | 22 |
| 13.61 | 6.5014 | 17 | 17.82 | 4.9734 | 12 | 12.45 | 7.1016 | 17 |
| 14.48 | 6.1120 | 14 | 18.40 | 4.8172 | 100 | 14.57 | 6.0731 | 17 |
| 14.94 | 5.9251 | 12 | 18.82 | 4.7114 | 41 | 17.02 | 5.2041 | 19 |
| 15.20 | 5.8243 | 12 | 19.23 | 4.6122 | 35 | 17.78 | 4.9856 | 20 |
| 16.05 | 5.5165 | 24 | 19.59 | 4.5282 | 33 | 18.41 | 4.8153 | 62 |
| 16.92 | 5.2359 | 11 | 20.96 | 4.2340 | 29 | 18.66 | 4.7514 | 34 |
| 18.26 | 4.8541 | 46 | 21.71 | 4.0901 | 32 | 19.22 | 4.6139 | 15 |

TABLE 5-continued

COMPLETE X-RAY DIFFRACTION PEAKS OF
FORM III, FORM IV AND FORM V OLANZAPINE
SUMMARY OF d-spacing AND I/I₁ INTENSITY RATIO

| FORM-III | | | FORM-IV | | | FORM-V | | |
|---|---|---|---|---|---|---|---|---|
| 2-theta (deg.) | d-spacing | I/I₁ | 2-theta (deg.) | d-spacing | I/I₁ | 2-theta (deg.) | d-spacing | I/I₁ |
| 18.66 | 4.7514 | 10 | 23.66 | 3.7574 | 23 | 19.58 | 4.5302 | 24 |
| 19.46 | 4.5578 | 24 | 24.04 | 3.6989 | 40 | 19.84 | 4.4714 | 51 |
| 19.74 | 4.4938 | 38 | 25.39 | 3.5052 | 11 | 20.99 | 4.2271 | 91 |
| 19.92 | 4.4536 | 36 | | | | 21.49 | 4.1307 | 40 |
| 20.84 | 4.2588 | 49 | | | | 21.80 | 4.0736 | 15 |
| 21.38 | 4.1523 | 30 | | | | 22.27 | 3.9880 | 31 |
| 21.82 | 4.0699 | 15 | | | | 23.54 | 3.7763 | 10 |
| 22.26 | 3.9898 | 52 | | | | 23.92 | 3.7167 | 62 |
| 22.81 | 3.8955 | 10 | | | | 25.20 | 3.5315 | 22 |
| 23.84 | 3.7288 | 42 | | | | 26.38 | 3.3762 | 13 |
| 24.97 | 3.5626 | 25 | | | | 29.70 | 3.0060 | 11 |
| 29.49 | 3.0262 | 18 | | | | | | |

What is claimed is:

1. A pharmaceutical composition comprising as an active ingredient at least one solid olanzapine polymorph selected from Form III olanzapine, Form IV olanzapine, Form V olanzapine, and salts and mixtures thereof; and one or more pharmaceutically acceptable carriers, excipients or diluents;

wherein Forms III, IV and V olanzapine are olanzapine polymorphs having typical x-ray powder diffraction patterns represented by the following interplanar spacings:

| FORM-III d-spacing (Å) | FORM-IV d-spacing (Å) | FORM IV d-spacing (Å) |
|---|---|---|
| 10.3156 | 9.9487 | 10.5932 |
| 7.1713 | 8.5074 | 10.2170 |
| 6.5014 | 8.2103 | 9.9503 |
| 5.5165 | 4.8172 | 8.5259 |
| 4.8541 | 4.7114 | 7.1016 |
| 4.5578 | 4.6122 | 6.0731 |
| 4.4938 | 4.5282 | 5.2041 |
| 4.4536 | 4.2340 | 4.9856 |
| 4.2588 | 4.0901 | 4.8153 |
| 3.9898 | 3.7574 | 4.7514 |
| 3.7288 | 3.6989 | 4.5302 |
| 3.5626 | | 4.4714 |
| 3.0262 | | 4.2271 |
| | | 4.1307 |
| | | 3.9880 |
| | | 3.7763 |
| | | 3.7167 |
| | | 3.5315. | and the composition is in the form of a suspension, emulsion, solid capsule, tablet, caplet, cachet, lozenge, troche, granular formulation or powdered formulation.

2. The pharmaceutical composition according to claim 1, wherein the olanzapine polymorph is Form III olanzapine.

3. The pharmaceutical composition according to claim 2, wherein the Form III olanzapine is further characterized bysubstantially the following x-ray powder diffraction pattern, wherein d represents the interplanar spacing and I/I₁ represents the typical relative intensities:

| d-spacing (Å) | I/I₁ |
|---|---|
| 10.3156 | 100 |
| 7.1713 | 16 |
| 6.5014 | 17 |
| 5.5165 | 24 |
| 4.8541 | 46 |
| 4.5578 | 24 |
| 4.4938 | 38 |
| 4.4536 | 36 |
| 4.2588 | 49 |
| 3.9898 | 52 |
| 3.7288 | 42 |
| 3.5626 | 25 |
| 3.0262 | 18. |

4. The pharmaceutical composition according to claim 2, wherein the Form III olanzapine is further characterized by having an infrared spectrum having absorbances at the following wavenumbers:
611
656
671
746
765
845
935
1369.

5. The pharmaceutical composition according to claim 1, wherein the olanzapine polymorph is Form IV olanzapine.

6. The pharmaceutical composition according to claim 5, wherein the Form IV olanzapine is further characterized by substantially the following x-ray powder diffraction pattern, wherein d represents the interplanar spacing and I/I₁ represents the typical relative intensities:

| d-spacing (Å) | I/I₁ |
|---|---|
| 9.9487 | 83 |
| 8.5074 | 15 |
| 8.2103 | 17 |
| 4.8172 | 100 |
| 4.7114 | 41 |

-continued

| d-spacing (Å) | I/I$_1$ |
|---|---|
| 4.6122 | 35 |
| 4.5282 | 33 |
| 4.2340 | 29 |
| 4.0901 | 32 |
| 3.7574 | 23 |
| 3.6989 | 40. |

7. The pharmaceutical composition according to claim 5, wherein the Form IV olanzapine is further characterized by having an infrared spectrum having absorbances at the following wavenumbers:
604
661
758
904
931
1365
1456.

8. The pharmaceutical composition according to claim 1, wherein the olanzapine polymorph is Form V olanzapine.

9. The pharmaceutical composition according to claim 8, wherein the Form V olanzapine is further characterized by substantially the following x-ray powder diffraction pattern, wherein d represents the interplanar spacing and I/I$_1$ represents the typical relative intensities:

| d-spacing (Å) | I/I$_1$ |
|---|---|
| 10.5932 | 17 |
| 10.2170 | 100 |
| 9.9503 | 57 |
| 8.5259 | 22 |
| 7.1016 | 17 |
| 6.0731 | 17 |
| 5.2041 | 19 |
| 4.9856 | 20 |
| 4.8153 | 62 |
| 4.7514 | 34 |
| 4.5302 | 24 |
| 4.4714 | 51 |
| 4.2271 | 91 |
| 4.1307 | 40 |
| 3.9880 | 31 |
| 3.7763 | 10 |
| 3.7167 | 62 |
| 3.5315 | 22. |

10. The pharmaceutical composition according to claim 8, wherein the Form V olanzapine is further characterized by having an infrared spectrum having absorbances at the following wavenumbers:
604
671
746
758
847
928
1357
1369.

11. A pharmaceutical composition containing as an active ingredient at least one solid olanzapine polymorph selected from Form III olanzapine, Form IV olanzapine, Form V olanzapine, and salts and mixtures thereof;
wherein Forms III, IV and V olanzapine are olanzapine polymorphs having typical x-ray powder diffraction patterns represented by the following interplanar spacings:

| FORM-III d-spacing (Å) | FORM-IV d-spacing (Å) | FORM-V d-spacing (Å) |
|---|---|---|
| 10.3156 | 9.9487 | 10.5932 |
| 7.1713 | 8.5074 | 10.2170 |
| 6.5014 | 8.2103 | 9.9503 |
| 5.5165 | 4.8172 | 8.5259 |
| 4.8541 | 4.7114 | 7.1016 |
| 4.5578 | 4.6122 | 6.0731 |
| 4.4938 | 4.5282 | 5.2041 |
| 4.4536 | 4.2340 | 4.9856 |
| 4.2588 | 4.0901 | 4.8153 |
| 3.9898 | 3.7574 | 4.7514 |
| 3.7288 | 3.6989 | 4.5302 |
| 3.5626 | | 4.4714 |
| 3.0262 | | 4.2271 |
| | | 4.1307 |
| | | 3.9880 |
| | | 3.7763 |
| | | 3.7167 |
| | | 3.5315 | and the composition is in the form of a suspension, emulsion, solid capsule, tablet, caplet, cachet, lozenge, troche, granular formulation or powdered formulation.

12. A method of treating a patient having a psychotic condition or mild anxiety comprising administering a therapeutically effective amount of at least one olanzapine polymorph to said patient;
wherein the at least one olanzapine polymorph is selected from Form III olanzapine, Form IV olanzapine, Form V olanzapine, and salts and mixtures thereof; and
wherein Forms III, IV and V olanzapine are olanzapine polymorphs having typical x-ray powder diffraction patterns represented by the following interplanar spacings:

| FORM-III d-spacing (Å) | FORM-IV d-spacing (Å) | FORM IV d-spacing (Å) |
|---|---|---|
| 10.3156 | 9.9487 | 10.5932 |
| 7.1713 | 8.5074 | 10.2170 |
| 6.5014 | 8.2103 | 9.9503 |
| 5.5165 | 4.8172 | 8.5259 |
| 4.8541 | 4.7114 | 7.1016 |
| 4.5578 | 4.6122 | 6.0731 |
| 4.4938 | 4.5282 | 5.2041 |
| 4.4536 | 4.2340 | 4.9856 |
| 4.2588 | 4.0901 | 4.8153 |
| 3.9898 | 3.7574 | 4.7514 |
| 3.7288 | 3.6989 | 4.5302 |
| 3.5626 | | 4.4714 |
| 3.0262 | | 4.2271 |
| | | 4.1307 |
| | | 3.9880 |
| | | 3.7763 |
| | | 3.7167 |
| | | 3.5315. |

13. The method according to claim 12, wherein the olanzapine polymorph is Form III olanzapine.

14. The method according to claim 12, wherein the olanzapine polymorph is Form IV olanzapine.

15. The method according to claim 12, wherein the olanzapine polymorph is Form V olanzapine.

16. A method of treating a patient having a psychotic condition selected from schizophrenia and schizophreniform disorders, acute mania, Bipolar I Disorder, psychotic mood disorder and psychosis associated with Alzheimer's disease comprising administering a therapeutically effective amount of at least one olanzapine polymorph to said patient;
wherein the at least one olanzapine polymorph is selected from Form III olanzapine, Form IV olanzapine, Form V olanzapine, and salts and mixtures thereof and
wherein Forms III, IV and V olanzapine are olanzapine polymorphs having typical x-ray powder diffraction patterns represented by the following interplanar spacings:

| FORM-III d-spacing (Å) | FORM-IV d-spacing (Å) | FORM IV d-spacing (Å) |
|---|---|---|
| 10.3156 | 9.9487 | 10.5932 |
| 7.1713 | 8.5074 | 10.2170 |
| 6.5014 | 8.2103 | 9.9503 |
| 5.5165 | 4.8172 | 8.5259 |
| 4.8541 | 4.7114 | 7.1016 |
| 4.5578 | 4.6122 | 6.0731 |
| 4.4938 | 4.5282 | 5.2041 |
| 4.4536 | 4.2340 | 4.9856 |
| 4.2588 | 4.0901 | 4.8153 |
| 3.9898 | 3.7574 | 4.7514 |
| 3.7288 | 3.6989 | 4.5302 |
| 3.5626 |  | 4.4714 |
| 3.0262 |  | 4.2271 |
|  |  | 4.1307 |
|  |  | 3.9880 |
|  |  | 3.7763 |
|  |  | 3.7167 |
|  |  | 3.5315. |

17. The method according to claim 16, wherein the olanzapine polymorph is Form III olanzapine.

18. The method according to claim 16, wherein the olanzapine polymorph is Form IV olanzapine.

19. The method according to claim 16, wherein the olanzapine polymorph is Form V olanzapine.

* * * * *